United States Patent
Bourque

(10) Patent No.: US 10,500,321 B2
(45) Date of Patent: *Dec. 10, 2019

(54) IMPLANTABLE BLOOD PUMP

(71) Applicant: TC1 LLC, St. Paul, MN (US)

(72) Inventor: Kevin Bourque, Reading, MA (US)

(73) Assignee: TC1 LLC, St. Paul, MN (US)

( * ) Notice: Subject to any disclaimer, the term of this patent is extended or adjusted under 35 U.S.C. 154(b) by 2 days.

This patent is subject to a terminal disclaimer.

(21) Appl. No.: 15/594,373

(22) Filed: May 12, 2017

(65) Prior Publication Data

US 2017/0246365 A1 Aug. 31, 2017

Related U.S. Application Data

(60) Division of application No. 14/735,990, filed on Jun. 10, 2015, now Pat. No. 9,675,741, which is a
(Continued)

(51) Int. Cl.
*A61M 1/12* (2006.01)
*A61M 1/10* (2006.01)
(Continued)

(52) U.S. Cl.
CPC .......... *A61M 1/1036* (2014.02); *A61M 1/101* (2013.01); *A61M 1/1015* (2014.02);
(Continued)

(58) Field of Classification Search
CPC .................................................. A61M 1/122
See application file for complete search history.

(56) References Cited

U.S. PATENT DOCUMENTS 845,816 A 3/1907 Prindle
888,654 A 5/1908 Prindle
(Continued)

FOREIGN PATENT DOCUMENTS

CN 300837668 10/2008
EP 150320 5/1990
(Continued)

OTHER PUBLICATIONS

Antaki et al., Pedia Flow TM Maglev Ventricular Assist Device: A Prescriptive Design Approach, Cardiovascular Engineering and Technology, vol. 1, No. 1, Mar. 2010, pp. 104-121.
(Continued)

*Primary Examiner* — Eric D. Bertram
(74) *Attorney, Agent, or Firm* — Kilpatrick Townsend and Stockton LLP

(57) ABSTRACT

A method for assisting blood circulation in a patient includes drawing a flow of blood from a patient's heart into a blood flow channel formed by a housing. The flow of blood is passed through a motor stator to a rotor disposed within the blood flow channel. The motor stator is arranged circumferentially around the blood flow channel. The rotor has permanent magnetic poles for magnetic levitation and rotation of the rotor. The motor stator is controlled to act as a radial bearing for magnetic levitation of the rotor and to rotate the rotor within the blood flow channel. The rotor is levitated within the blood flow channel in the direction of the rotor axis of rotation via passive magnetic interaction between the rotor and the motor stator. The flow of blood is output from the blood flow channel to the patient.

16 Claims, 6 Drawing Sheets

Related U.S. Application Data continuation of application No. 13/212,813, filed on Aug. 18, 2011, now Pat. No. 9,091,271.

(60) Provisional application No. 61/375,504, filed on Aug. 20, 2010.

(51) Int. Cl.
*F04D 13/06* (2006.01)
*F04D 29/048* (2006.01)

(52) U.S. Cl.
CPC ........ *A61M 1/1029* (2014.02); *A61M 1/1031* (2014.02); *A61M 1/1086* (2013.01); *A61M 1/122* (2014.02); *A61M 1/127* (2013.01); *F04D 13/064* (2013.01); *F04D 13/0606* (2013.01); *F04D 13/0633* (2013.01); *F04D 13/0646* (2013.01); *F04D 29/048* (2013.01); *A61M 1/1008* (2014.02); *A61M 1/1012* (2014.02); *A61M 2205/3365* (2013.01); *Y10T 29/49009* (2015.01)

(56) References Cited

U.S. PATENT DOCUMENTS

| | | | |
|---|---|---|---|
| 1,026,101 | A | 5/1912 | Marsh |
| 2,128,988 | A | 9/1938 | Russell |
| 2,747,512 | A | 5/1956 | Paul |
| 2,864,552 | A | 12/1958 | Norman |
| 3,005,117 | A | 10/1961 | Buchhold |
| 3,066,849 | A | 12/1962 | Beams |
| 3,122,101 | A | 2/1964 | Baker et al. |
| 3,225,608 | A | 12/1965 | Ivan |
| 3,401,640 | A | 9/1968 | John et al. |
| 3,499,274 | A | 3/1970 | Fergason |
| 3,575,536 | A | 4/1971 | Jacobs et al. |
| 3,597,022 | A | 8/1971 | Waldron |
| 3,608,088 | A | 9/1971 | Dorman et al. |
| 3,611,815 | A | 10/1971 | Fischell |
| 3,647,324 | A | 3/1972 | Rafferty et al. |
| 3,650,581 | A | 3/1972 | Boden et al. |
| 3,938,913 | A | 2/1976 | Isenberg et al. |
| 3,957,389 | A | 5/1976 | Rafferty et al. |
| 4,082,376 | A | 4/1978 | Wehde et al. |
| 4,135,253 | A | 1/1979 | Reich et al. |
| 4,213,207 | A | 7/1980 | Wilson |
| 4,340,260 | A | 7/1982 | Forster et al. |
| 4,382,199 | A | 5/1983 | Isaacson |
| 4,398,773 | A | 8/1983 | Boden et al. |
| 4,405,286 | A | 9/1983 | Studer |
| 4,408,966 | A | 10/1983 | Maruyama |
| 4,475,866 | A | 10/1984 | Kambe et al. |
| 4,507,048 | A | 3/1985 | Belenger et al. |
| 4,589,822 | A | 5/1986 | Clausen et al. |
| 4,642,036 | A | 2/1987 | Young |
| 4,688,998 | A | 8/1987 | Olsen et al. |
| 4,704,121 | A | 11/1987 | Moise |
| 4,763,032 | A | 8/1988 | Bramm et al. |
| 4,779,614 | A | 10/1988 | Moise |
| 4,844,707 | A | 7/1989 | Kletschka |
| 4,876,492 | A | 10/1989 | Lester et al. |
| 4,878,831 | A | 11/1989 | Ewing |
| 4,929,158 | A | 5/1990 | Girault |
| 4,944,748 | A | 7/1990 | Bramm et al. |
| 4,957,504 | A | 9/1990 | Chardack |
| 5,055,005 | A | 10/1991 | Kletschka |
| 5,078,741 | A | 1/1992 | Bramm et al. |
| 5,106,273 | A | 4/1992 | Lemarquand et al. |
| 5,112,200 | A | 5/1992 | Isaacson et al. |
| 5,112,202 | A | 5/1992 | Oshima et al. |
| 5,126,612 | A | 6/1992 | Girault |
| 5,127,792 | A | 7/1992 | Katsuta et al. |
| 5,159,219 | A | 10/1992 | Chu et al. |
| 5,177,387 | A | 1/1993 | Mcmichael et al. |
| 5,195,877 | A | 3/1993 | Kletschka |
| 5,220,232 | A | 6/1993 | Rigney, II et al. |
| 5,341,059 | A | 8/1994 | Fukuyama et al. |
| 5,360,317 | A | 11/1994 | Clausen et al. |
| 5,385,581 | A | 1/1995 | Bramm et al. |
| 5,470,208 | A | 11/1995 | Kletschka |
| 5,678,306 | A | 10/1997 | Bozeman, Jr. et al. |
| 5,708,346 | A | 1/1998 | Schob |
| 5,725,357 | A | 3/1998 | Nakazeki et al. |
| 5,798,454 | A | 8/1998 | Nakazeki et al. |
| 5,808,437 | A | 9/1998 | Schob |
| 5,917,297 | A | 6/1999 | Gerster et al. |
| 5,928,131 | A | 7/1999 | Prem |
| 5,947,703 | A | 9/1999 | Nojiri et al. |
| 6,053,705 | A | 4/2000 | Schob et al. |
| 6,100,618 | A | 8/2000 | Schoeb et al. |
| 6,130,494 | A | 10/2000 | Schob |
| 6,146,325 | A | 11/2000 | Lewis et al. |
| 6,222,290 | B1 | 4/2001 | Schob et al. |
| 6,227,797 | B1 | 5/2001 | Watterson et al. |
| 6,234,772 | B1 | 5/2001 | Wampler et al. |
| 6,244,835 | B1 * | 6/2001 | Antaki .................... F04D 3/005 415/900 |
| 6,249,067 | B1 | 6/2001 | Schob et al. |
| 6,264,635 | B1 | 7/2001 | Wampler et al. |
| 6,278,251 | B1 | 8/2001 | Schöb |
| 6,293,901 | B1 | 9/2001 | Prem |
| 6,302,661 | B1 | 10/2001 | Khanwilkar et al. |
| 6,351,048 | B1 | 2/2002 | Schob et al. |
| 6,355,998 | B1 | 3/2002 | Schob et al. |
| 6,394,769 | B1 | 5/2002 | Bearnson et al. |
| 6,447,266 | B2 | 9/2002 | Antaki et al. |
| 6,468,041 | B2 | 10/2002 | Ozaki |
| 6,559,567 | B2 | 5/2003 | Schob |
| 6,575,717 | B2 | 6/2003 | Ozaki et al. |
| 6,589,030 | B2 | 7/2003 | Ozaki |
| 6,605,032 | B2 | 8/2003 | Benkowski et al. |
| 6,623,475 | B1 | 9/2003 | Siess |
| 6,626,644 | B2 | 9/2003 | Ozaki |
| 6,634,224 | B1 | 10/2003 | Schob et al. |
| 6,640,617 | B2 | 11/2003 | Schob et al. |
| 6,641,378 | B2 | 11/2003 | Davis et al. |
| 6,688,861 | B2 | 2/2004 | Wampler |
| 6,707,200 | B2 | 3/2004 | Carroll et al. |
| 6,711,943 | B1 | 3/2004 | Schob |
| 6,817,836 | B2 | 11/2004 | Nose et al. |
| 6,949,066 | B2 | 9/2005 | Bearnson et al. |
| 7,070,398 | B2 | 7/2006 | Olsen et al. |
| 7,112,903 | B1 | 9/2006 | Schob |
| 7,138,776 | B1 | 11/2006 | Gauthier et al. |
| 7,150,711 | B2 | 12/2006 | Nüsser et al. |
| D534,548 | S | 1/2007 | Urano et al. |
| 7,160,242 | B2 | 1/2007 | Yanai |
| 7,229,258 | B2 | 6/2007 | Wood et al. |
| 7,229,474 | B2 | 6/2007 | Hoffmann et al. |
| 7,239,098 | B2 | 7/2007 | Masino |
| 7,284,956 | B2 | 10/2007 | Nose et al. |
| 7,338,521 | B2 | 3/2008 | Antaki et al. |
| 7,462,019 | B1 | 12/2008 | Allarie et al. |
| 7,497,116 | B2 | 3/2009 | Miyakoshi et al. |
| 7,511,443 | B2 | 3/2009 | Townsend et al. |
| 7,578,782 | B2 | 8/2009 | Miles et al. |
| 7,591,777 | B2 | 9/2009 | Larose |
| 7,645,225 | B2 | 1/2010 | Medvedev et al. |
| 7,699,588 | B2 | 4/2010 | Mendler |
| 7,854,631 | B2 | 12/2010 | Townsendl et al. |
| 7,861,582 | B2 | 1/2011 | Miyakoshi et al. |
| 7,887,479 | B2 | 2/2011 | Larose et al. |
| 7,951,062 | B2 | 5/2011 | Morello |
| 7,976,271 | B2 | 7/2011 | Larose et al. |
| 8,152,493 | B2 | 4/2012 | Larose et al. |
| 8,157,720 | B2 | 4/2012 | Marseille et al. |
| 8,303,482 | B2 | 11/2012 | Schima et al. |
| 8,382,830 | B2 | 2/2013 | Maher et al. |
| 8,506,470 | B2 | 8/2013 | Larose et al. |
| 8,517,699 | B2 | 8/2013 | Horvath |
| 8,556,795 | B2 | 10/2013 | Bolyard et al. |
| 8,597,350 | B2 | 12/2013 | Rudser et al. |
| 8,764,621 | B2 | 7/2014 | Badstibner et al. |
| 8,870,739 | B2 | 10/2014 | Larose et al. |

(56) References Cited

U.S. PATENT DOCUMENTS

| | | | |
|---|---|---|---|
| 8,882,477 B2 | 11/2014 | Fritz, IV et al. | |
| 8,956,275 B2 | 2/2015 | Bolyard et al. | |
| 9,091,271 B2* | 7/2015 | Bourque | A61M 1/101 |
| 2003/0021683 A1 | 1/2003 | Capone et al. | |
| 2004/0236420 A1 | 11/2004 | Yamane et al. | |
| 2005/0004421 A1 | 1/2005 | Pacella et al. | |
| 2005/0025630 A1 | 2/2005 | Ayre et al. | |
| 2005/0135948 A1 | 6/2005 | Olsen et al. | |
| 2005/0147512 A1 | 7/2005 | Chen et al. | |
| 2007/0100196 A1 | 5/2007 | Larose et al. | |
| 2009/0064755 A1 | 3/2009 | Fleischli et al. | |
| 2009/0234447 A1 | 9/2009 | Larose et al. | |
| 2010/0130809 A1 | 5/2010 | Morello | |
| 2010/0150749 A1 | 6/2010 | Horvath | |
| 2010/0152526 A1 | 6/2010 | Pacella et al. | |
| 2010/0241223 A1 | 9/2010 | Lee et al. | |
| 2010/0327687 A1 | 12/2010 | Iannello et al. | |
| 2011/0002794 A1 | 1/2011 | Haefliger et al. | |
| 2011/0031836 A1 | 2/2011 | Nussbaumer | |
| 2011/0054239 A1 | 3/2011 | Sutton et al. | |
| 2011/0071337 A1 | 3/2011 | Thompson et al. | |
| 2011/0144413 A1 | 6/2011 | Foster | |
| 2011/0187217 A1 | 8/2011 | Nussbaumer | |
| 2011/0237863 A1 | 9/2011 | Ricci et al. | |
| 2011/0245582 A1 | 10/2011 | Zafirelis et al. | |
| 2011/0313237 A1 | 12/2011 | Miyakoshi et al. | |
| 2012/0035411 A1 | 2/2012 | Larose et al. | |
| 2012/0046514 A1 | 2/2012 | Bourque | |
| 2012/0059212 A1 | 3/2012 | Larose et al. | |
| 2012/0134832 A1 | 5/2012 | Wu | |
| 2012/0226097 A1 | 9/2012 | Smith et al. | |
| 2012/0245680 A1* | 9/2012 | Masuzawa | A61M 1/1086 623/3.11 |
| 2012/0245681 A1 | 9/2012 | Casas et al. | |
| 2012/0253103 A1 | 10/2012 | Robert | |
| 2012/0310036 A1 | 12/2012 | Peters et al. | |
| 2013/0331934 A1 | 12/2013 | Kabir et al. | |
| 2014/0100413 A1 | 4/2014 | Casas et al. | |
| 2014/0194985 A1 | 7/2014 | Vadala, Jr. | |
| 2014/0275723 A1 | 9/2014 | Fritz, IV et al. | |
| 2014/0303426 A1 | 10/2014 | Kerkhoffs et al. | |
| 2014/0357937 A1 | 12/2014 | Reyes et al. | |
| 2015/0051438 A1 | 2/2015 | Taskin | |

FOREIGN PATENT DOCUMENTS

| | | |
|---|---|---|
| EP | 60569 | 12/1990 |
| EP | 378251 | 6/1994 |
| EP | 2357374 | 8/2011 |
| GB | 1491710 | 11/1977 |
| JP | 01257792 | 10/1989 |
| JP | 02016390 | 1/1990 |
| JP | 03088996 | 4/1991 |
| JP | 04148095 | 5/1992 |
| JP | 2000510929 | 8/2000 |
| JP | 2002512333 | 4/2002 |
| JP | 2003093500 | 4/2003 |
| JP | D1373017 | 10/2009 |
| JP | 2011530315 | 12/2011 |
| TW | D136032 | 7/2010 |
| WO | 9953974 | 10/1999 |
| WO | 2005032620 | 4/2005 |
| WO | 2006137496 | 12/2006 |
| WO | 2010015836 | 2/2010 |
| WO | 2010023815 | 3/2010 |
| WO | 2010036815 | 4/2010 |
| WO | 2012028181 | 3/2012 |

OTHER PUBLICATIONS

Barletta et al., Design of a bearing less blood pump, Proc.3rd Int. Symp. on Magnetic Suspension Technology, Dec. 13-15, 1995, pp. 265-274.

Izraelev et al., A Pasively-Suspended Tesla Pump Left Ventricular Assist Device, NIH Public Access, vol. 55, No. 6, 2009, pp. 556-561.

* cited by examiner

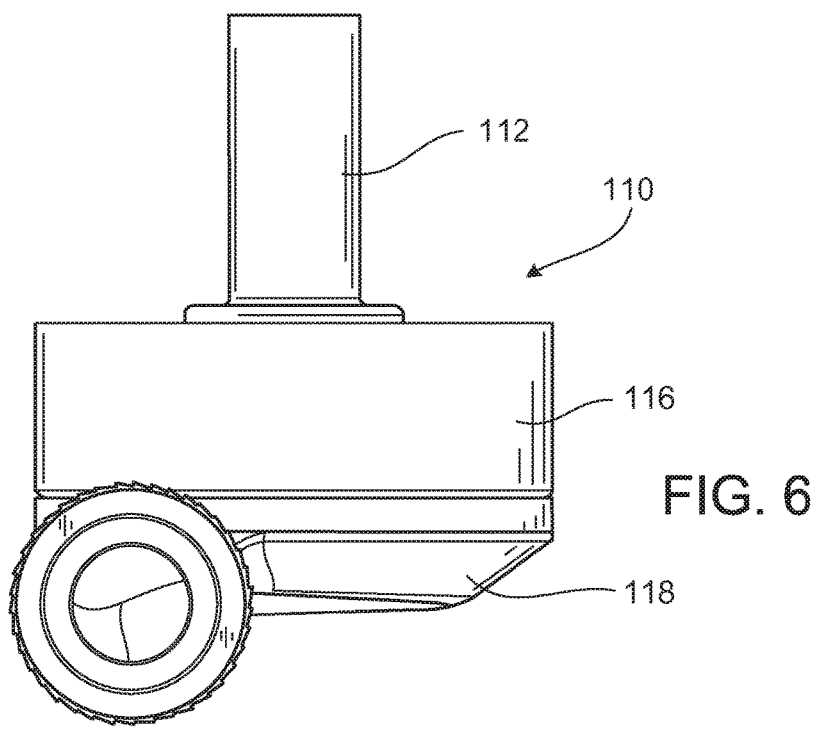
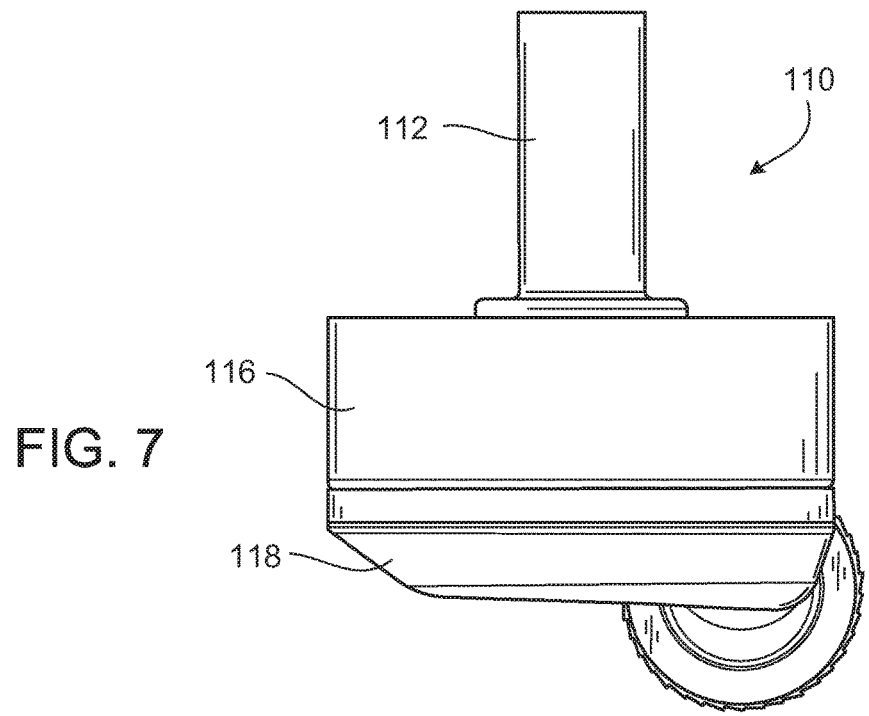

IMPLANTABLE BLOOD PUMP

CROSS-REFERENCES TO RELATED APPLICATIONS

This application is a divisional of U.S. application Ser. No. 14/735,990, filed Jun. 10, 2015, now U.S. Pat. No. 9,675,741, issued Jun. 13, 2017, and titled "Implantable Blood Pump," which application is a continuation application of U.S. application Ser. No. 13/212,813, filed Aug. 18, 2011, now U.S. Pat. No. 9,091,271, issued Jul. 28, 2015, and titled "Implantable Blood Pump," which application claims the benefit of U.S. Provisional Application Ser. No. 61/375,504, filed Aug. 20, 2010, and titled "Implantable Blood Pump," the entire contents of which are incorporated herein by reference in their entirety.

FIELD

This description relates to implantable blood pumps.

BACKGROUND

Ventricular assist devices, known as VADs, are implantable blood pumps used for both short-term and long-term applications where a patient's heart is incapable of providing adequate circulation. For example, a patient suffering from heart failure may use a VAD while awaiting a heart transplant. In another example, a patient may use a VAD while recovering from heart surgery. Thus, a VAD can supplement a weak heart or can effectively replace the natural heart's function. VADs can be implanted in the patient's body and powered by an electrical power source outside the patient's body.

BRIEF SUMMARY

In one general aspect, an implantable blood pump includes a housing and a blood flow conduit. Within the housing, the blood pump includes a stator located about the blood flow conduit and a magnetically-levitated rotor.

In another general aspect, an implantable blood pump includes a housing defining an inlet opening and an outlet opening. Within the housing, a dividing wall defines a blood flow conduit extending between the inlet opening and the outlet opening of the housing. The blood pump has a rotary motor that includes a stator and a rotor. The stator is disposed within the housing circumferentially about the dividing wall such that the inner blood flow conduit extends through the stator.

In another general aspect, an implantable blood pump includes a puck-shaped housing having a first face defining an inlet opening, a peripheral sidewall, and a second face opposing the first face. The blood pump has an internal dividing wall defining an inner blood flow conduit extending between the inlet opening and an outlet opening of the housing. The puck-shaped housing has a thickness from the first face to the second face that is less than a width of the housing between opposing portions of the peripheral sidewall. The blood pump also has a motor having a stator and a rotor. The stator is disposed in the housing circumferentially about the blood flow conduit and includes magnetic levitation components operable to control an axial position and a radial position of the rotor. The rotor is disposed in the inner blood flow conduit and includes an impeller operable to pump blood from the inlet opening to the outlet opening through at least a portion of the magnetic levitation components of the stator.

Implementations of the above aspects may include one or more of the following features. For example, the stator is disposed circumferentially about at least a part of the rotor and is positioned relative to the rotor such that in use blood flows within the blood flow conduit through the stator before reaching the rotor. The rotor has permanent magnetic poles for magnetic levitation of the rotor. A passive magnetic control system is configured to control an axial position of the rotor relative to the stator, and an active electromagnetic control system is configured to radially center the rotor within the inner blood flow conduit. An electromagnetic control system controls at least one of a radial position and an axial position of the rotor relative to the stator, and the electromagnetic control system has control electronics located within the housing about the dividing wall.

The control electronics are located between the inlet opening and the stator. The control electronics can be configured to control the active magnetic control system. The rotor has only one magnetic moment. The stator includes a first coil for driving the rotor and a second coil for controlling a radial position of the rotor, and the first coil and the second coil are wound around a first pole piece of the stator. The housing has a first face that defines the inlet opening, a second face opposing the first face, and a peripheral wall extending from the first face to the second face. The housing includes a rounded transition from the second face to the peripheral wall. The housing defines a volute located such that in use blood flows within the blood flow conduit through the stator before reaching the volute. The volute can be located between the stator and the second face. The housing can also include a cap that includes the second face, defines at least part of the volute, and defines at least part of the outlet. The cap is engaged with the peripheral wall of the housing. The housing also includes an inlet cannula extending from the first face and in fluid communication with the inlet opening. The inlet cannula can be inserted into the patient's heart. The outlet opening is defined in the second face and/or the peripheral wall. A thickness of the housing between the first face and the second face is less than a width of the housing.

In another general aspect, a method includes inserting a puck-shaped blood pump housing into a patient's body. The blood pump is inserted such that an opening defined in a first flat face of the housing that is proximate to a stator of the blood pump faces the patient's heart. Additionally, the blood pump is inserted such that a second rounded face of the housing that is proximate to an impeller of the blood pump faces away from the patient's heart. The first face is disposed against a portion of the patient's heart such that the second face of the housing faces away from the heart of the patient. In some implementations, the method includes inserting an inlet cannula of the housing into the patient's heart.

In another general aspect, making a blood pump includes assembling a motor stator and control electronics in a puck-shaped housing circumferentially about an internal dividing wall. The internal dividing wall defines an inner blood flow conduit that extends from an inlet opening to an outlet opening of the housing. The stator is assembled in the housing such that the inner blood flow conduit extends through the motor stator. Disposed within the inner blood flow conduit is a magnetically-levitated rotor. The rotor is surrounded by the stator such that impeller blades carried by the rotor are downstream of the stator from the inlet opening.

In use, the impeller pumps blood from the inlet opening to the outlet opening through the stator.

Implementations may include one or more of the following features. For example, the rotor has only one magnetic moment. The stator includes at least one first coil for driving the rotor and at least one second coil for controlling a radial position of the rotor, the at least one first coil and the at least one second coil being wound around a first pole piece of the stator. The housing includes a first face that defines the inlet opening, and further comprising engaging an end cap with a peripheral wall of the housing, the end cap including a second face, defining at least part of a volute, and defining at least part of the outlet opening. The housing includes a rounded transition from the second face to the peripheral wall. The housing further includes an inlet cannula extending from the first face and in fluid communication with the inlet opening. A thickness of the housing between the first face and the second face is less than a width of the housing.

In another general aspect, a method of pumping blood includes magnetically rotating a centrifugal pump impeller of a blood pump device to draw blood from a patient's heart through an inlet opening of a housing of the blood pump device into an inner blood flow conduit within a stator in the housing, through the inner blood flow conduit, and through an outlet opening of the housing. The method includes selectively controlling a radial position of the impeller within the inner blood flow conduit.

The details of one or more implementations are set forth in the accompanying drawings and the description below. Other features will be apparent from the description and drawings, and from the claims.

BRIEF DESCRIPTION OF THE DRAWINGS

FIG. 6 is a front view of the blood pump of FIG. 4.

FIG. 7 is a back view of the blood pump of FIG. 4.

DETAILED DESCRIPTION

Figure 1:
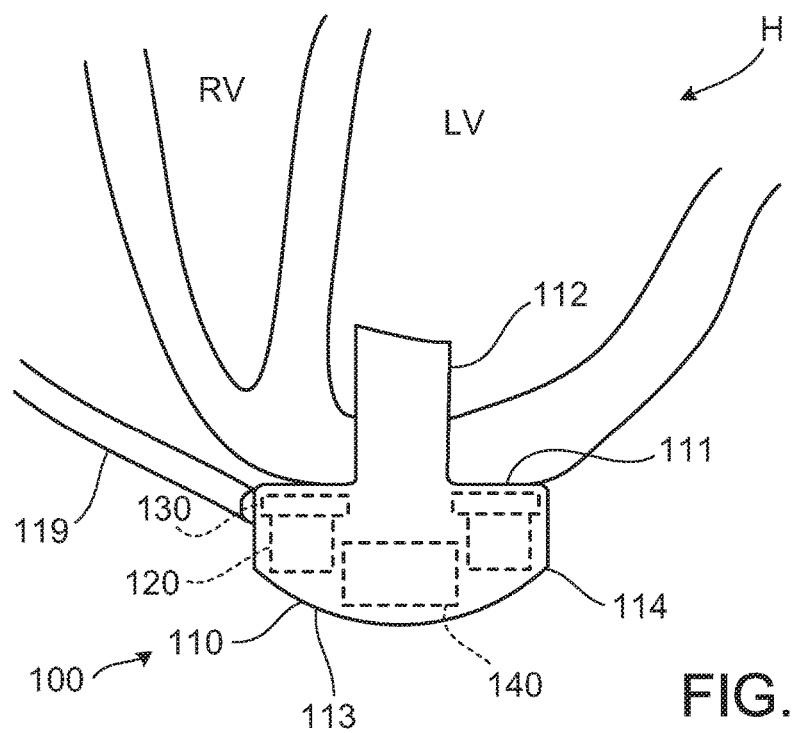
FIG. 1 is an illustration of a blood pump in a use position implanted in a patient's body.

With reference to FIGS. 1 and 4-11, a left ventricular assist blood pump 100 having a puck-shaped housing 110 is implanted in a patient's body with a first face 111 of the housing 110 positioned against the patient's heart H and a second face 113 of the housing 110 facing away from the heart H. The first face 111 of the housing 110 includes an inlet cannula 112 extending into the left ventricle LV of the heart H. The second face 113 of the housing 110 has a chamfered edge 114 to avoid irritating other tissue that may come into contact with the blood pump 100, such as the patient's diaphragm. To construct the illustrated shape of the puck-shaped housing 110 in a compact form, a stator 120 and electronics 130 of the pump 100 are positioned on the inflow side of the housing toward first face 111, and a rotor 140 of the pump 100 is positioned along the second face 113.

This positioning of the stator 120, electronics 130, and rotor 140 permits the edge 114 to be chamfered along the contour of the rotor 140, as illustrated in at least FIGS. 2, 4, and 6-9, for example.

Figure 2:
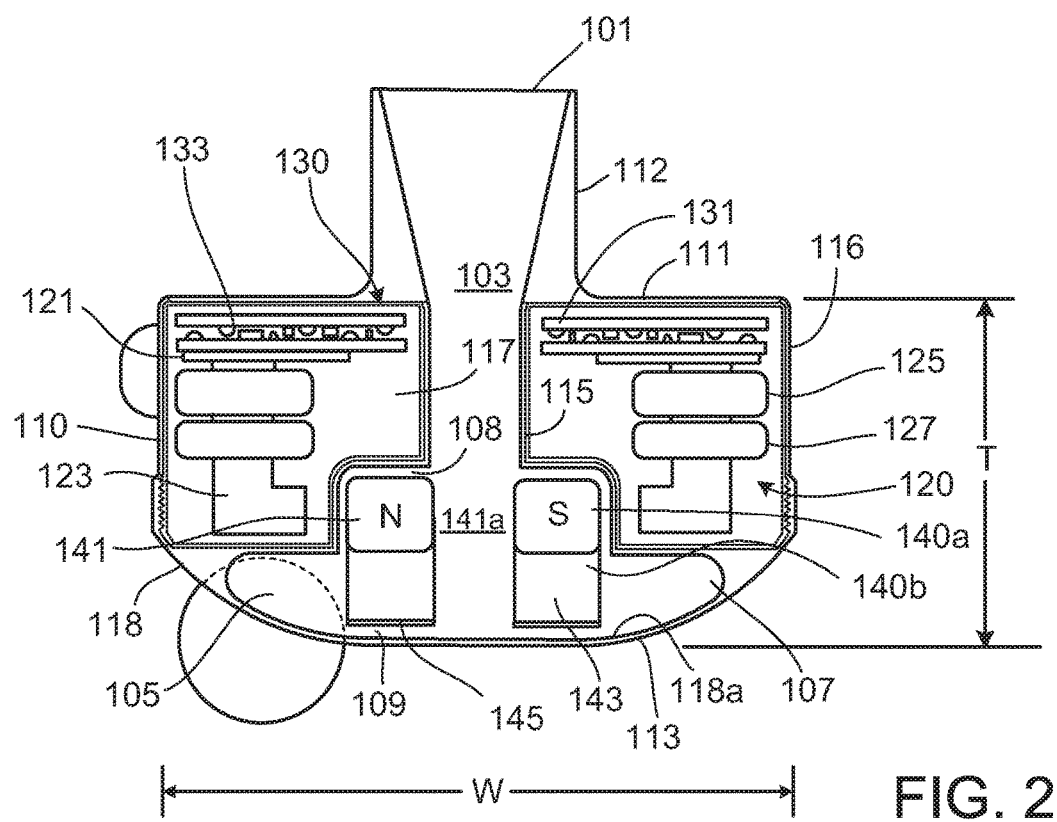
FIG. 2 is a cross-sectional view of the blood pump of FIG. 1.

Referring to FIG. 2, the blood pump 100 includes a dividing wall 115 within the housing 110 defining a blood flow conduit 103. The blood flow conduit 103 extends from an inlet opening 101 of the inlet cannula 112 through the stator 120 to an outlet opening 105 defined by the housing 110. The rotor 140 is positioned within the blood flow conduit 103. The stator 120 is disposed circumferentially about a first portion 140a of the rotor 140, for example about a permanent magnet 141. The stator 120 is also positioned relative to the rotor 140 such that, in use, blood flows within the blood flow conduit 103 through the stator 120 before reaching the rotor 140. The permanent magnet 141 has a permanent magnetic north pole N and a permanent magnetic south pole S for combined active and passive magnetic levitation of the rotor 140 and for rotation of the rotor 140. The rotor 140 also has a second portion 140b that includes impeller blades 143. The impeller blades 143 are located within a volute 107 of the blood flow conduit such that the impeller blades 143 are located proximate to the second face 113 of the housing.

The puck-shaped housing 110 further includes a peripheral wall 116 that extends between the first face 111 and a removable cap 118. As illustrated, the peripheral wall 116 is formed as a hollow circular cylinder having a width W between opposing portions of the peripheral wall 116. The housing 110 also has a thickness T between the first face 111 and the second face 113 that is less than the width W. The thickness T is from about 0.5 inches to about 1.5 inches, and the width W is from about 1 inch to about 4 inches. For example, the width W can be approximately 2 inches, and the thickness T can be approximately 1 inch.

The peripheral wall 116 encloses an internal compartment 117 that surrounds the dividing wall 115 and the blood flow conduit 103, with the stator 120 and the electronics 130 disposed in the internal compartment 117 about the dividing wall 115. The removable cap 118 includes the second face 113, the chamfered edge 114, and defines the outlet opening 105. The cap 118 can be threadably engaged with the peripheral wall 116 to seal the cap 118 in engagement with the peripheral wall 116. The cap 118 includes an inner surface 118a of the cap 118 that defines the volute 107 that is in fluid communication with the outlet opening 105.

Within the internal compartment 117, the electronics 130 are positioned adjacent to the first face 111 and the stator 120 is positioned adjacent to the electronics 130 on an opposite side of the electronics 130 from the first face 111. The electronics 130 include circuit boards 131 and various components 133 carried on the circuit boards 131 to control the operation of the pump 100 by controlling the electrical supply to the stator 120. The housing 110 is configured to receive the circuit boards 131 within the internal compartment 117 generally parallel to the first face III for efficient use of the space within the internal compartment 117. The circuit boards also extend radially-inward towards the dividing wall 115 and radially-outward towards the peripheral wall 116. For example, the internal compartment 117 is generally sized no larger than necessary to accommodate the circuit boards 131, and space for heat dissipation, material expansion, potting materials, and/or other elements used in installing the circuit boards 131. Thus, the external shape of the housing 110 proximate the first face 111 generally fits the shape of the circuits boards 131 closely to provide external dimensions that are not much greater than the dimensions of the circuit boards 131.

Figure 3:
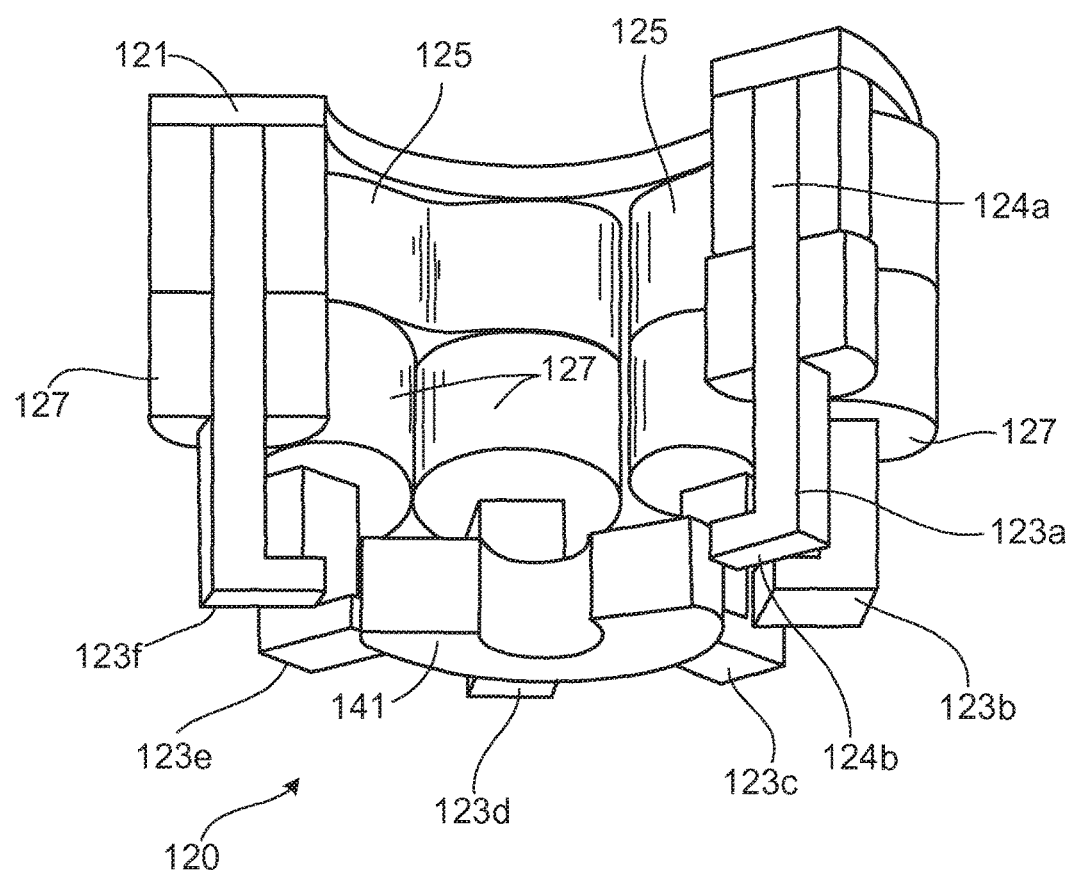
FIG. 3 is a partial cut-away perspective view of a stator of a blood pump.
Figure 4:
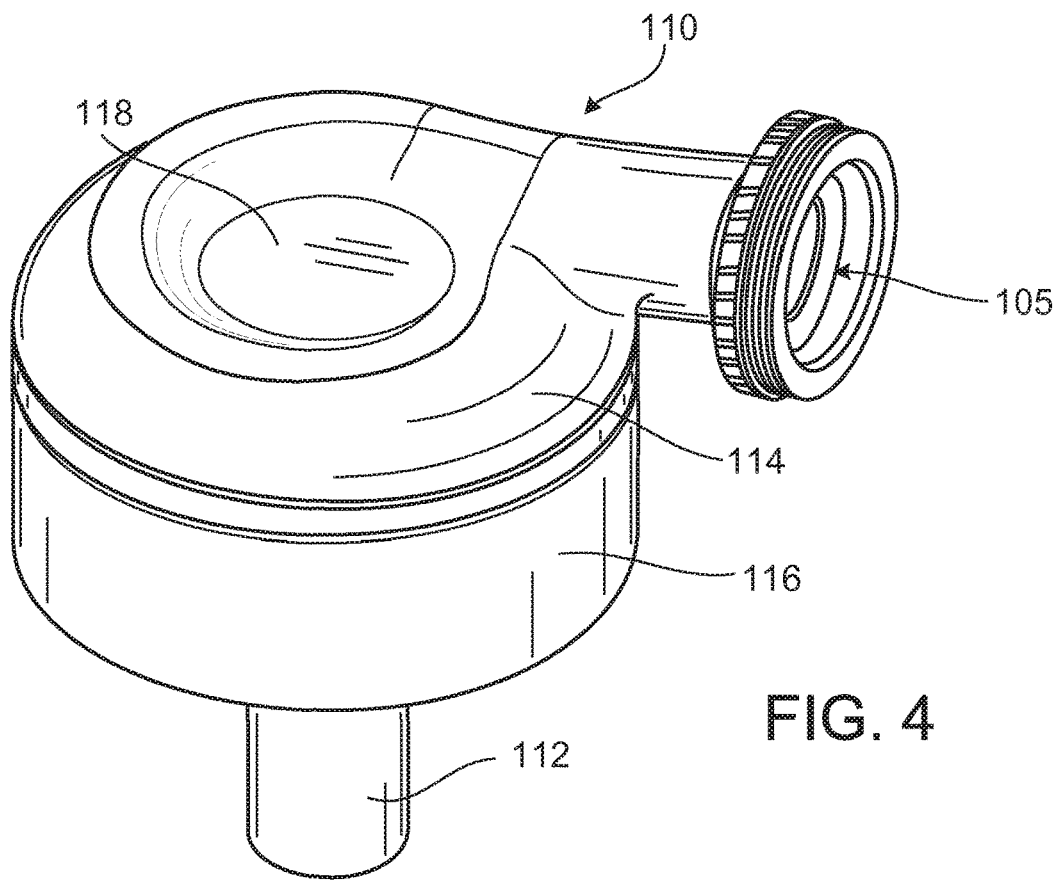
FIG. 4 is a bottom perspective view of a blood pump.
Figure 5:
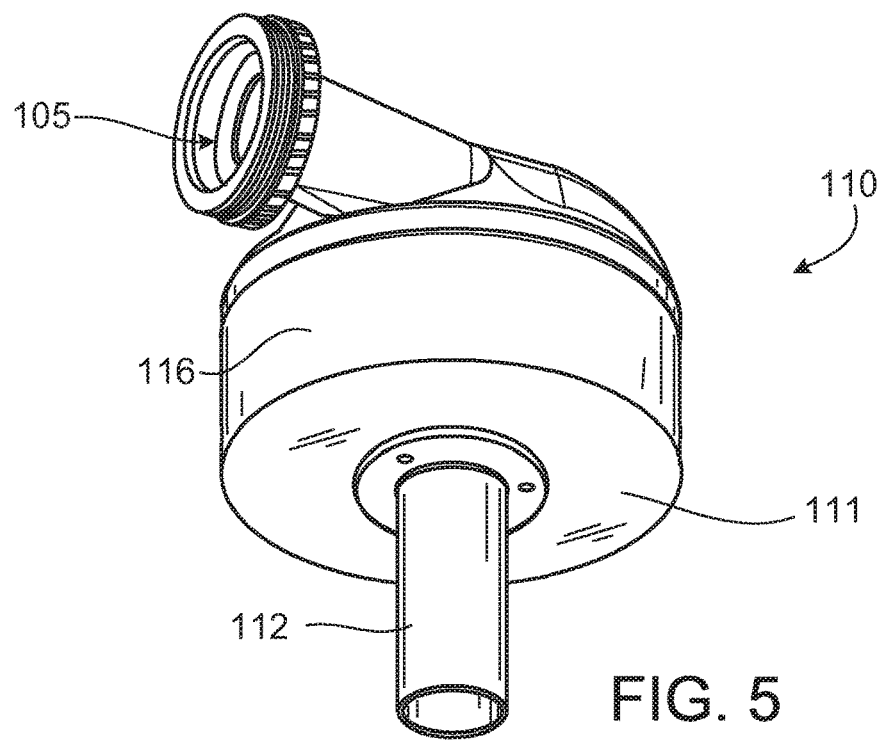
FIG. 5 is a top perspective view of the blood pump of FIG. 4.
Figure 8:
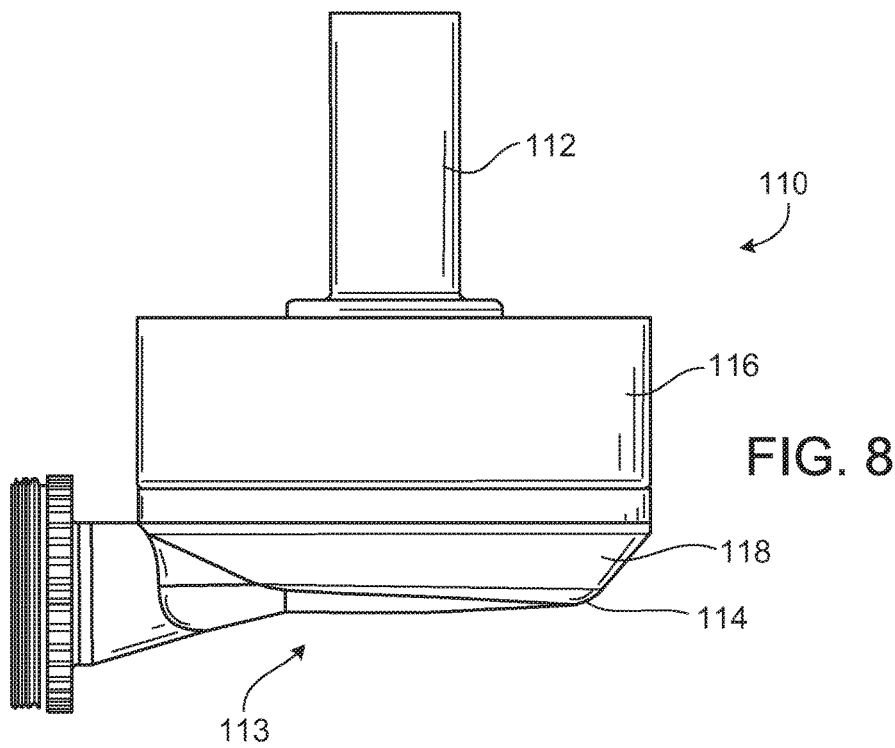
FIG. 8 is a right side view of the blood pump of FIG. 4.
Figure 9:
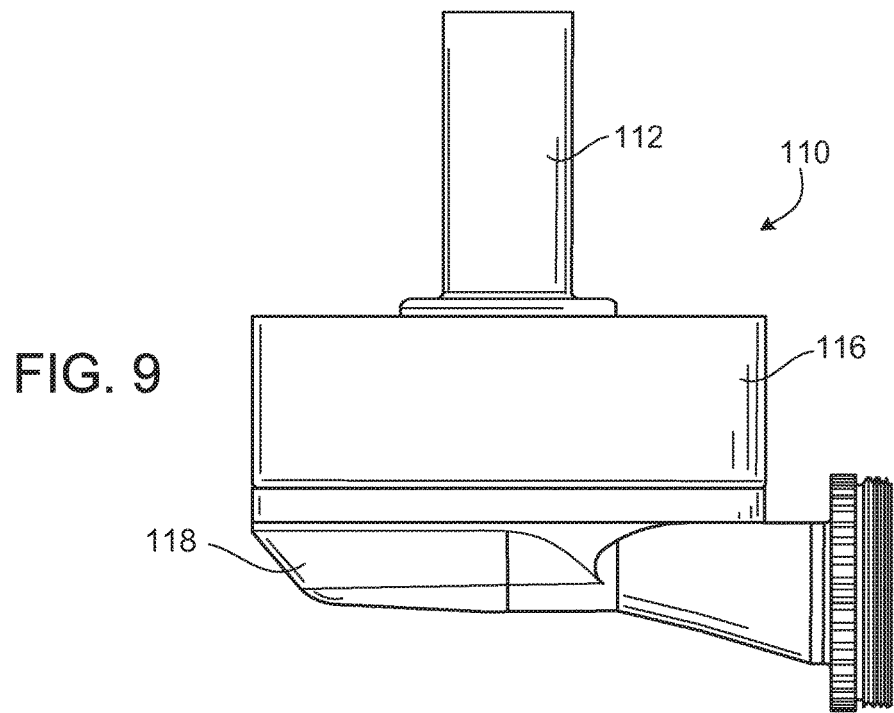
FIG. 9 is a left side view of the blood pump of FIG. 4.
Figure 10:
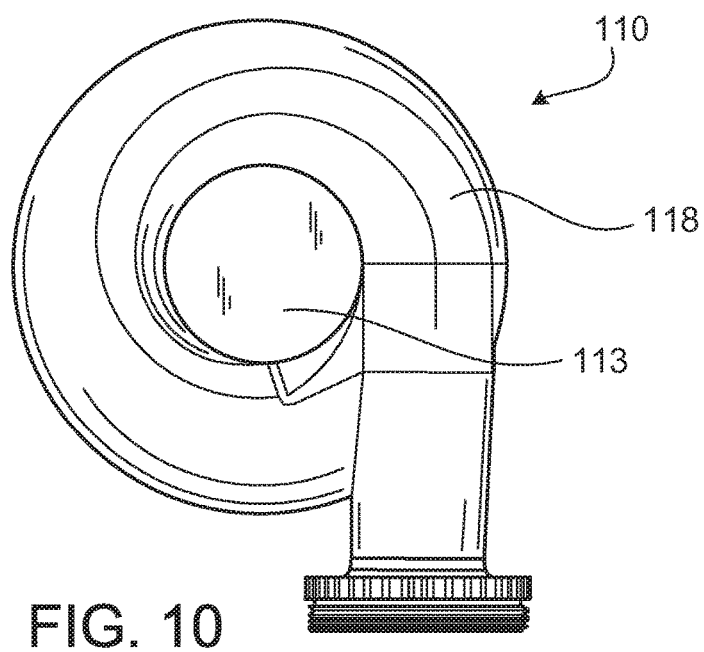
FIG. 10 is a bottom view of the blood pump of FIG. 4.
Figure 11:
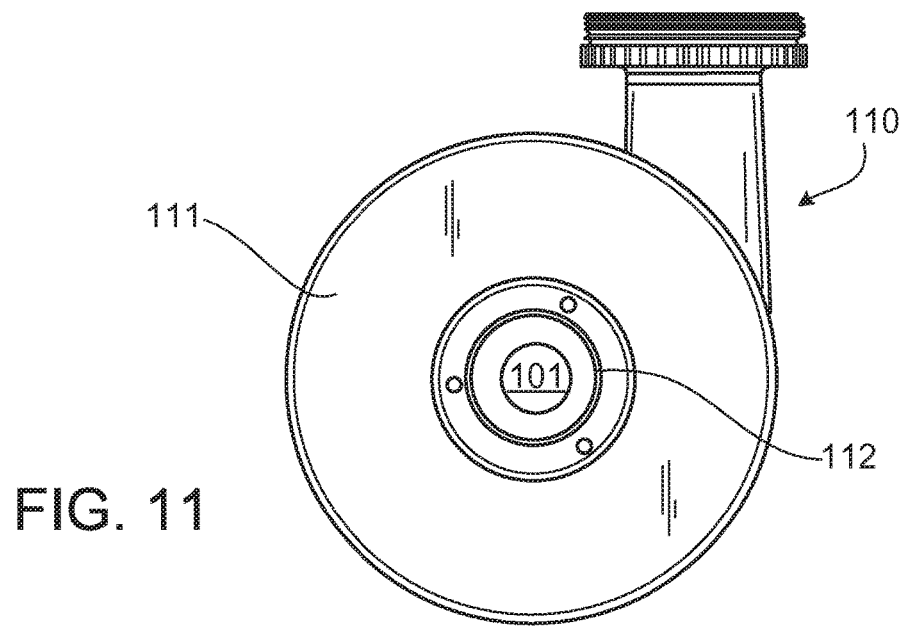
FIG. 11 is a top view of the blood pump of FIG. 4.

With continued reference to FIG. 2 and with reference to FIG. 3, the stator 120 includes a back iron 121 and pole pieces 123a-123f arranged at intervals around the dividing wall 115. The back iron 121 extends around the dividing wall 115 and is formed as a generally flat disc of a ferromagnetic material, such as steel, in order to conduct magnetic flux. The back iron 121 is arranged beside the control electronics 130 and provides a base for the pole pieces 123a-123f.

Each of the pole piece 123a-123f is L-shaped and has a drive coil 125 for generating an electromagnetic field to rotate the rotor 140. For example, the pole piece 123a has a first leg 124a that contacts the back iron 121 and extends from the back iron 121 towards the second face 113. The pole piece 123a also has a second leg 124b that extends from the first leg 124a towards the dividing wall 115 proximate the location of the permanent magnet 141 of the rotor 140. Each of the pole pieces 123a-123f also has a levitation coil 127 for generating an electromagnetic field to control the radial position of the rotor 140.

Each of the drive coils 125 and the levitation coils 127 includes multiple windings of a conductor around the pole pieces 123a-123f. Particularly, each of the drive coils 125 is wound around two adjacent ones of the pole pieces 123, such as pole pieces 123d and 123e, and each levitation coil 127 is wound around a single pole piece. The drive coils 125 and the levitation coils 127 are wound around the first legs of the pole pieces 123, and magnetic flux generated by passing electrical current though the coils 125 and 127 during use is conducted through the first legs and the second legs of the pole pieces 123 and the back iron 121. The drive coils 125 and the levitation coils 127 of the stator 120 are arranged in opposing pairs and are controlled to drive the rotor and to radially levitate the rotor 140 by generating electromagnetic fields that interact with the permanent magnetic poles S and N of the permanent magnet 141. Because the stator 120 includes both the drive coils 125 and the levitation coils 127, only a single stator is needed to levitate the rotor 140 using only passive and active magnetic forces. The permanent magnet 141 in this configuration has only one magnetic moment and is formed from a monolithic permanent magnetic body 141. For example, the stator 120 can be controlled as discussed in U.S. Pat. No. 6,351,048, the entire contents of which are incorporated herein by reference. The control electronics 130 and the stator 120 receive electrical power from a remote power supply via a cable 119 (FIG. 1).

The rotor 140 is arranged within the housing 110 such that its permanent magnet 141 is located upstream of impeller blades in a location closer to the inlet opening 101. The permanent magnet 141 is received within the blood flow conduit 103 proximate the second legs 124b of the pole pieces 123 to provide the passive axial centering force though interaction of the permanent magnet 141 and ferromagnetic material of the pole pieces 123. The permanent magnet 141 of the rotor 140 and the dividing wall 115 form a gap 108 between the permanent magnet 141 and the dividing wall 115 when the rotor 140 is centered within the dividing wall 115. The gap 108 may be from about 0.2 millimeters to about 2 millimeters. For example, the gap 108 is approximately 1 millimeter. The north permanent magnetic pole N and the south permanent magnetic pole S of the permanent magnet 141 provide a permanent magnetic attractive force between the rotor 140 and the stator 120 that acts as a passive axial centering force that tends to maintain the rotor 140 generally centered within the stator 120 and tends to resist the rotor 140 from moving towards the first face 111 or towards the second face 113. When the gap 108 is smaller, the magnetic attractive force between the permanent magnet 141 and the stator 120 is greater, and the gap 108 is sized to allow the permanent magnet 141 to provide the passive magnetic axial centering force having a magnitude that is adequate to limit the rotor 140 from contacting the dividing wall 115 or the inner surface 118a of the cap 118. The rotor 140 also includes a shroud 145 that covers the ends of the impeller blades 143 facing the second face 113 that assists in directing blood flow into the volute 107. The shroud 145 and the inner surface 118a of the cap 118 form a gap 109 between the shroud 145 and the inner surface 118a when the rotor 140 is levitated by the stator 120. The gap 109 is from about 0.2 millimeters to about 2 millimeters. For example, the gap 109 is approximately 1 millimeter.

As blood flows through the blood flow conduit 103, blood flows through a central aperture 141a formed through the permanent magnet 141. Blood also flows through the gap 108 between the rotor 140 and the dividing wall 115 and through the gap 109 between the shroud 145 and the inner surface 108a of the cap 118. The gaps 108 and 109 are large enough to allow adequate blood flow to limit clot formation that may occur if the blood is allowed to become stagnant. The gaps 108 and 109 are also large enough to limit pressure forces on the blood cells such that the blood is not damaged when flowing through the pump 100. As a result of the size of the gaps 108 and 109 limiting pressure forces on the blood cells, the gaps 108 and 109 are too large to provide a meaningful hydrodynamic suspension effect. That is to say, the blood does not act as a bearing within the gaps 108 and 109, and the rotor is only magnetically-levitated.

Because the rotor 140 is radially suspended by active control of the levitation coils 127 as discussed above, and because the rotor 140 is axially suspended by passive interaction of the permanent magnet 141 and the stator 120, no rotor levitation components are needed proximate the second face 113. The incorporation of all the components for rotor levitation in the stator 120 (i.e., the levitation coils 127 and the pole pieces 123) allows the cap 118 to be contoured to the shape of the impeller blades 143 and the volute 107. Additionally, incorporation of all the rotor levitation components in the stator 120 eliminates the need for electrical connectors extending from the compartment 117 to the cap 118, which allows the cap to be easily installed and/or removed and eliminates potential sources of pump failure.

In use, the drive coils 125 of the stator 120 generates electromagnetic fields through the pole pieces 123 that selectively attract and repel the magnetic north pole N and the magnetic south pole S of the rotor 140 to cause the rotor 140 to rotate within stator 120. As the rotor 140 rotates, the impeller blades 143 force blood into the volute 107 such that blood is forced out of the outlet opening 105. Additionally, the rotor draws blood into pump 100 through the inlet opening 101. As blood is drawn into the blood pump by rotation of the impeller blades 143 of the rotor 140, the blood flows through the inlet opening 101 and flows through the control electronics 130 and the stator 120 toward the rotor 140. Blood flows through the aperture 141a of the permanent magnet 141 and between the impeller blades 143, the shroud 145, and the permanent magnet 141, and into the volute 107. Blood also flows around the rotor 140, through the gap 108 and through the gap 109 between the shroud 145 and the inner surface 118a of the cap 118. The blood exits the volute 107 through the outlet opening 105.

A number of implementations have been described. Nevertheless, it will be understood that various modifications may be made without departing from the spirit and scope of the claimed invention. For example, the cap 118 can be engaged with the peripheral wall 116 using a different attachment mechanism or technique, including snap-fit engagement, adhesives, or welding. Additionally, while the cap 118 has been described as defining the outlet opening 105 and the chamfered edge 114, the outlet opening 105 and/or the chamfered edge 114 can be defined by the peripheral wall 116 or by both the peripheral wall 116 and the cap 118. Similarly, the dividing wall 115 can be formed as part of the cap 118.

Additionally, the rotor 140 can include two or more permanent magnets. The number and configuration of the pole pieces 123 can also be varied. The operation of the control electronics 130 is selected to account for the number and position of pole pieces of the stator and permanent magnets of the rotor. Also, the cap 118 can be engaged with the peripheral wall using other techniques, such as adhesives, welding, snap-fit, shrink-fit, or other technique or structure. Similarly, the first face Ill may be formed from a separate piece of material than the peripheral wall 116 and the first face 111, including the inlet cannula 112, can be attached to the peripheral wall 116, such as by welding, after the control electronics 130 and the stator 120 have been mounted in the internal compartment 117. The shroud 145 may be omitted and optionally replaced by other flow control devices to achieve a desired pump efficiency. As another option, the control electronics 130 can be located external to the pump 100, such as in a separate housing implanted in the patient's abdomen, or external to the patient's body.

In some implementations, the dimensions of the housing 110 can be larger or smaller than those described above. Similarly, the ratio of the width W of the housing 110 to the thickness T of the housing can be different than the ratio described above. For example, the width W can be from about 1.1 to about 5 times greater than the thickness T. Additionally, the permanent magnet 141 of the rotor 140 can include two or more pairs of north and south magnetic poles. While the peripheral wall 116 and the dividing wall 115 are illustrated as cylinders having circular cross-sectional shapes, one or both can alternatively be formed having other cross-sectional shapes, such as oval, or an irregular shape. Similarly, the peripheral wall 116 can be tapered such that the housing does not have a constant width W from the first face Ill to the second face 113.

As mentioned above, in some implementations, the blood pump 100 can be used to assist a patient's heart during a transition period, such as during a recovery from illness and/or surgery or other treatment. In other implementations, the blood pump 100 can be used to partially or completely replace the function of the patient's heart on a generally permanent basis, such as where the patient's aortic valve is surgically sealed.

Accordingly, other embodiments are within the scope of the following claims.

What is claimed is:

1. A method for assisting blood circulation in a patient, the method comprising:
   drawing a flow of blood from a patient's heart into a blood flow channel formed by a housing;
   passing the flow of blood through a motor stator to a rotor disposed within the blood flow channel, the motor stator being arranged circumferentially around the blood flow channel, the rotor having permanent magnetic poles for magnetic levitation and rotation of the rotor;
   passing a first portion of the flow of blood through a central aperture formed through the rotor;
   passing a second portion of the flow of blood through a gap formed between the rotor and the housing;
   controlling delivery of current to the motor stator to control a radial position of the rotor within the blood flow channel and to control rotation of the rotor within the blood flow channel, the rotor being rotated around a rotor axis of rotation;
   levitating the rotor within the blood flow channel in the direction of the rotor axis of rotation via only a passive magnetic interaction between the rotor and the motor stator; and
   outputting the flow of blood from the blood flow channel to the patient.

2. The method of claim 1, wherein the motor stator axially overlaps the permanent magnetic poles of the rotor with respect to the rotor axis of rotation.

3. The method of claim 1, wherein the motor stator comprises a back iron and a plurality of pole pieces supported by the back iron, the back iron being configured to conduct magnetic flux and having an aperture through which the blood flow channel passes.

4. The method of claim 3, further comprising supporting control electronics within the housing and between the back iron and the patient's heart, the control electronics being configured to control the delivery of current to the motor stator for controlling the rotation and radial levitation of the rotor within the blood flow channel.

5. The method of claim 1, wherein the rotor and housing are configured and the delivery of current to the motor stator is controlled such that the gap between the rotor and the housing is between about 0.2 mm to about 2 mm.

6. The method of claim 1, comprising impelling the first portion of the flow of blood via impeller blades of the rotor to force the flow of blood from the blood flow channel to the patient.

7. The method of claim 6, wherein:
   the first portion of the flow of blood is impelled substantially centrifugally via the rotor; and
   the flow of blood is output from the blood flow channel in a direction transverse to the rotor axis of rotation.

8. The method of claim 1, wherein the rotor is levitated within the blood flow channel in the direction of the rotor axis of rotation such that the rotor is separated from the housing in the direction of the rotor axis of rotation via axial gaps between about 0.2 mm to about 2 mm.

9. A method for assisting blood circulation in a patient, the method comprising:
   drawing a flow of blood from a patient's heart into a blood flow channel formed by a housing;
   passing the flow of blood through a motor stator to a rotor disposed within the blood flow channel, the motor stator being arranged circumferentially around the blood flow channel, the rotor having permanent magnetic poles for magnetic levitation and rotation of the rotor;
   passing a first portion of the flow of blood through a central aperture formed through the rotor;
   passing a second portion of the flow of blood through a gap formed between the rotor and the housing;
   controlling the motor stator to act as a radial bearing for magnetic levitation of the rotor and to rotate the rotor within the blood flow channel, levitating the rotor within the blood flow channel in the direction of the rotor axis of rotation via only a passive magnetic interaction between the rotor and the motor stator; and outputting the flow of blood from the blood flow channel to the patient.

10. The method of claim 9, wherein the motor stator axially overlaps the permanent magnetic poles of the rotor with respect to the rotor axis of rotation.

11. The method of claim 9, wherein the motor stator comprises a back iron and a plurality of pole pieces supported by the back iron, the back iron being configured to conduct magnetic flux and having an aperture through which the blood flow channel passes.

12. The method of claim 11, further comprising supporting control electronics within the housing and between the back iron and the patient's heart, the control electronics being configured to control the delivery of current to the motor stator for controlling the rotation and radial levitation of the rotor within the blood flow channel.

13. The method of claim 9, wherein the rotor and housing are configured and the delivery of current to the motor stator is controlled such that the gap between the rotor and the housing is between about 0.2 mm to about 2 mm.

14. The method of claim 9, comprising impelling the first portion of the flow of blood via impeller blades of the rotor to force the flow of blood from the blood flow channel to the patient.

15. The method of claim 14, wherein:
the first portion of the flow of blood is impelled substantially centrifugally via the rotor; and
the flow of blood is output from the blood flow channel in a direction transverse to the rotor axis of rotation.

16. The method of claim 9, wherein the rotor is levitated within the blood flow channel in the direction of the rotor axis of rotation such that the rotor is separated from the housing in the direction of the rotor axis of rotation via axial gaps between about 0.2 mm to about 2 mm.

* * * * *